United States Patent [19]

Myers

[11] Patent Number: 5,020,528

[45] Date of Patent: Jun. 4, 1991

[54] METHOD AND APPARATUS FOR PERMITTING MEDICAL PERSONNEL TO ATTEND TO A PATIENT SITUATED IN A HAZARDOUS LOCATION REMOTE THEREFROM

[76] Inventor: Phillip R. Myers, 6060 Brook Dr., Falls Church, Va. 22044

[21] Appl. No.: 530,410

[22] Filed: May 30, 1990

[51] Int. Cl.$^5$ .............................................. A61B 5/04
[52] U.S. Cl. ................................. 128/202.13; 128/696
[58] Field of Search ................. 128/419 D, 630, 696, 128/746, 200.24, 202.13, 202.27, 202.28, 204.21-204.23, 205.26; 600/21, 22; 174/47, 65 R, 67

[56] References Cited

U.S. PATENT DOCUMENTS

| | | | |
|---|---|---|---|
| 2,502,707 | 11/1942 | Mejean | 128/202.27 |
| 3,253,588 | 5/1966 | Vuilleumier et al. | 128/696 |
| 3,571,486 | 3/1971 | Kennedy | 174/11 R |
| 3,871,371 | 3/1975 | Weigl | 128/204.017 |
| 3,923,055 | 12/1975 | Hammacher | 128/204.23 |
| 3,961,624 | 6/1976 | Weigl | 128/204.017 |
| 4,140,114 | 2/1979 | Moore et al. | 128/201.019 |
| 4,297,999 | 11/1981 | Kitrell | 128/205.016 |
| 4,506,665 | 3/1985 | Andrews et al. | 128/202.27 |
| 4,651,746 | 3/1987 | Wall | 128/670 |
| 4,834,103 | 5/1989 | Heath | 128/298 |

Primary Examiner—William E. Kamm
Attorney, Agent, or Firm—Shlesinger Arkwright & Garvey

[57] ABSTRACT

An apparatus for permitting medical personnel to attend to an injured individual situated in a hazardous area from a remote location. The apparatus includes a first end adapted to be located at a position remote from the injured individual and a second end adapted to be located at a position adjacent the individual. The first end includes a first connector for connecting a health aid storage unit and a monitoring unit to the first end. The second end includes a second connector for connecting a health aid administering unit and a sensor unit to the second end. A corrugated tubular member extends from the first end to the second end and includes first and second transmission lines. The first transmission line transmits a health aid from the health air storage unit to the health aid administering unit. The second transmission line transmits a signal from a sensor unit to a monitoring unit indicating at least one physiological condition of the patient.

20 Claims, 2 Drawing Sheets

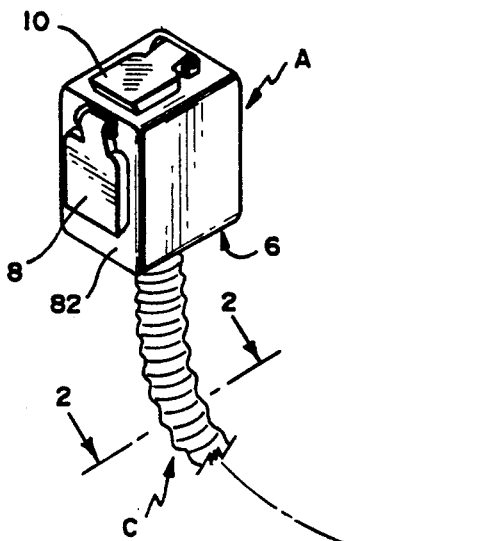
FIG_1
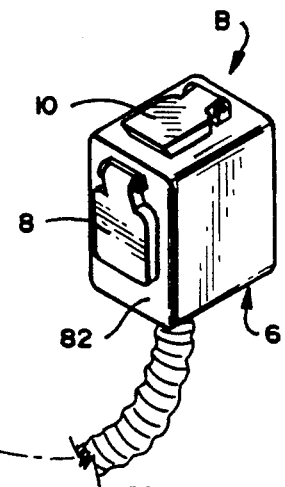
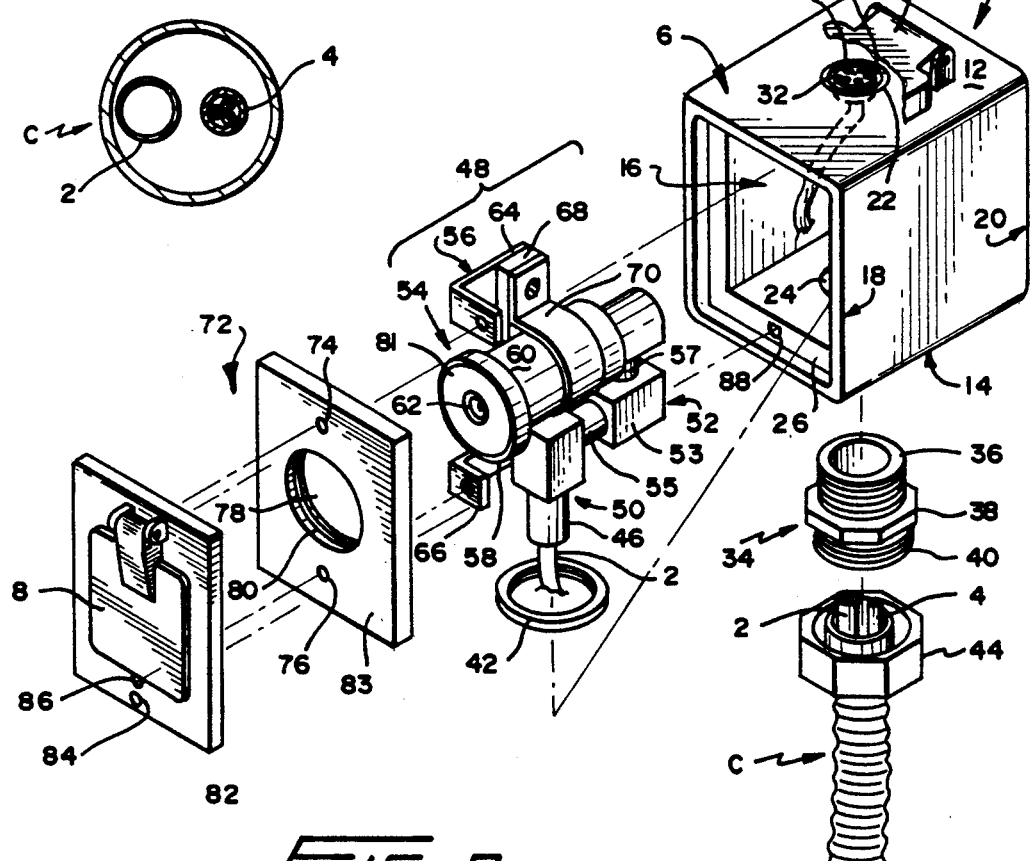
FIG_2
FIG_3

METHOD AND APPARATUS FOR PERMITTING MEDICAL PERSONNEL TO ATTEND TO A PATIENT SITUATED IN A HAZARDOUS LOCATION REMOTE THEREFROM

FIELD OF THE INVENTION

The present invention generally relates to a method and apparatus for permitting medical personnel to attend to a patient located in a hazardous area.

BACKGROUND OF THE INVENTION

In previously known techniques for treating injured persons situated in a hazardous area, medical personnel have administered assistance to the individual in the hazardous area. Also, it has been necessary for medical personnel to transport equipment such as oxygen storage tanks, electrocardiogram monitoring units and the like into the hazardous area. There are numerous disadvantages inherent in treating patients in this manner.

For example, previously where an individual requiring medical attention was trapped in a partially collapsed building, underground passageway or the like, medical personnel remained in the partially collapsed structure to administer the necessary treatment to the individual. Since the attending medical personnel were in the collapsed structure for a prolonged period of time, it was more likely that they would be seriously injured due to a further collapse of the structure. Also, commonly under these circumstances medical personnel were required to traverse partially supported or unsupported terrain to reach the individual needing medical assistance. The additional weight of the equipment and the personnel to carry the same significantly increased the risk of further collapse of the structure resulting in injury to the person or persons trapped therein as well as the assisting medical personnel.

Another example of where medical personnel must administer aid to an individual located in a hazardous region is when a tractor trailer hauling a toxic substance is involved in an accident injuring the driver or any passengers therein. If the toxic substance is leaking from the trailer compartment, the area immediately surrounding the trailer is designated a "hot" zone. In this zone, the harmful effects or the toxic substance are greatest and thus the time an individual remains in this area must be kept to a minimum. The area removed from the tractor trailer a distance sufficient to render negligible the harmful effects of the toxic substance is designated as the "safe" zone. The area between the "safe" zone and the "hot" zone is designated as the "warm" zone. Conventionally, medical personnel appropriately attired entered the "hot" zone and immediately moved any individuals needing medical attention to the "warm" zone where the appropriate assistance was administered. Equipment such as oxygen tanks and electrocardiogram monitoring units were positioned adjacent the patient in the "warm" zone. Thus, these techniques exposed the medical personnel as well as the equipment to the harmful effects of the toxic substance. Although the medical personnel are appropriately attired, they may still encounter some side effects from the toxic substance. Furthermore, the equipment positioned in the "warm" zone becomes contaminated and must later be discarded. Accordingly, significant expenditures must be made to replace the contaminated equipment.

It is readily apparent from the above discussion that conventional techniques for rendering medical assistance to persons located in a hazardous region endanger the safety of the attending medical personnel as well as the person or persons needing medical care. Additionally, these techniques may result in the destruction of costly medical equipment.

OBJECTS AND SUMMARY OF THE INVENTION

An object of the present invention is to provide a method and apparatus for permitting medical personnel to attend to a patient located in a hazardous area free from the disadvantages inherent in previously known techniques for accomplishing the same.

Another object of the present invention is to provide a method and apparatus which permit medical personnel to administer aid to an individual situated in a hazardous area from a remote location.

A further object of the present invention is to provide a method and apparatus which permits medical personnel to monitor at least one physiological condition of an individual situated in a hazardous area from a remote location.

Still a further object of the present invention is to provide an apparatus with interchangeable ends thereby permitting the assisting personnel to position either end adjacent an injured person.

Yet another object of the present invention is to provide a method and apparatus which significantly reduces the time it takes medical personnel to reach an individual located in a hazardous region.

A further object of the present invention is to provide a method and apparatus which minimizes the likelihood of medical personnel being injured while attending to a person situated in a hazardous area.

Yet another object of the present invention is to provide a method and apparatus which minimizes the likelihood of medical equipment such as oxygen tanks, electrocardiogram monitoring units and the like from becoming damaged while medical personnel are attending to an individual located in a hazardous area.

Another object of the present invention is to provide a method and apparatus which significantly reduces the amount of medical equipment which must be transported to a location adjacent an individual situated in a hazardous area.

Still another object of the present invention is to provide a method and apparatus which permits medical personnel to accurately and reliably administer aid and monitor the physiological conditions of an individual located in a hazardous area.

Other objects and advantages of the present invention will be readily apparent from the following detailed description thereof.

In summary, the present invention is directed to an apparatus for permitting medical personnel to attend to an injured individual from a remote location. The apparatus includes a first end adapted to be located at a position remote from and a second end adapted to be located at a position adjacent the injured individual. The first end includes a first connector for connecting a health aid storage unit and a monitoring unit to the first end. The second end includes a second connector for connecting a health aid administering unit and a sensor unit to the second end. A corrugated tubular member extends from the first end to the second end and includes first and second transmitting lines. The first transmitting line transmits a health aid from the health aid storage unit to the health aid administering unit. Health aid is defined as anything which is administered to an individual to maintain or improve his health. This includes but is not limited to providing the individual with oxygen, anesthesia, medicine and the like. The second transmission line transmits a signal from a sensor unit to a monitoring unit indicating at least one physiological condition of the individual.

DETAILED DESCRIPTION OF THE DRAWINGS

FIG. 1 is a fragmentary perspective view of the preferred embodiment of the present invention.

FIG. 2 is a cross-sectional view taken along lines 2—2 in FIG. 1.

FIG. 3 is an exploded view of one end of the preferred embodiment of the present invention.

DETAILED DESCRIPTION OF THE INVENTION

Figure 4:
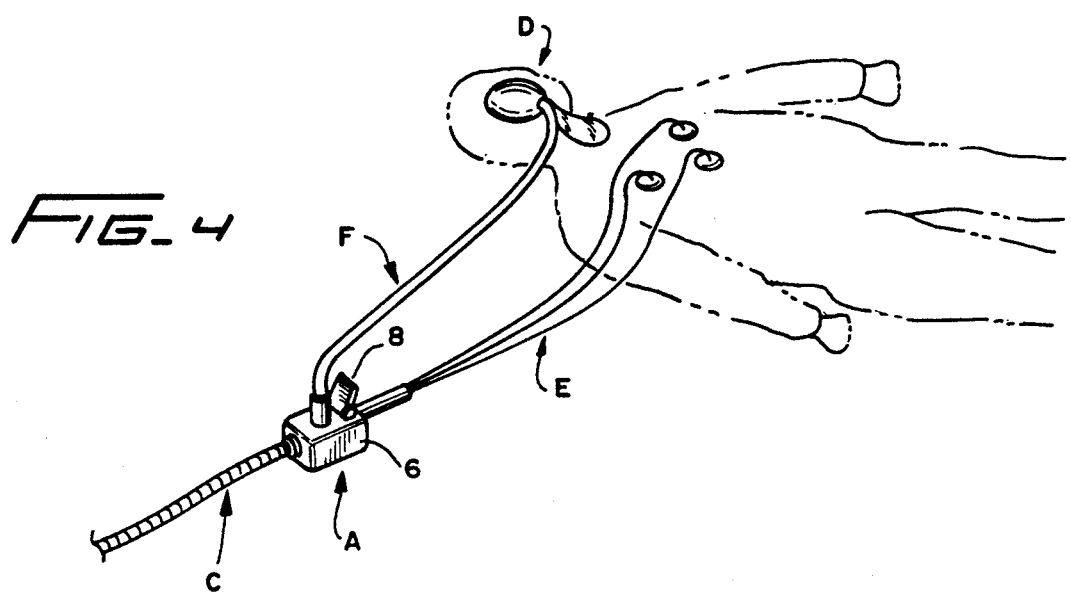
FIG. 4 is a perspective view of one end of the preferred embodiment of the present invention connected to an oxygen administering unit and a sensor unit.

The preferred embodiment of the present invention will now be described.

FIGS. 1 THROUGH 3

Referring to FIG. 1, the preferred embodiment of the present invention includes a first end A, a second end B and a corrugated tubular member C connecting ends A and B. The tubular member C has a substantially circular cross-section and houses a conductive oxygen line 2 and a three-lead cable 4. The oxygen line 2 and three-lead cable 4 are of a conventional construction. Preferably, tubular member C has a length of approximately 50 feet. However, it will be readily appreciated that this may be varied to accommodate differing needs. The tubular member c can be formed from any suitable flexible material.

Referring to FIG. 3, first end A includes a housing 6 and rubber-lined flip-lid covers 8 and 10. The housing 6 is constructed from a rubber similar to that marketed by Woodhead Industries, Inc. under the trademark NEoTEX. The rubber-lined flip-lid covers 8 and 10 are also of the type manufactured by Woodhead Industries, Inc. The rubber housing 6 includes upper and lower surfaces 12 and 14, respectively. The housing 6 further includes a substantially rectangularly shaped opening 16 extending from the front edge 18 to the rear edge 20 thereof. A substantially circular opening 22 is formed in upper surface 12. A substantially circular opening 24 is also formed in the lower surface 14. The opening 24 has a diameter greater than that of opening 22. The front and rear faces of housing 6 each have a recessed lip 26 formed therein (only the lip in the front face is shown).

A female connecting plug 28 is positioned in opening 22. Plug 28 includes a support collar and a plurality of conventional fasteners (not shown) for securing the same to the underside of upper surface 12. Annular recess 30 and a plurality of openings 32 are formed in plug 28 to receive a conventional six-pin male connector. Plug 28 is of the type distributed by Physio-Control, Inc., under Part No. 801050-01.

A threaded connector 34 includes a first threaded portion 36, a hexagonal collar 38, and second threaded portion 40. The first threaded portion 36 is inserted into opening 24 such that collar 38 abuts lower surface 14. Annular ring 42 is threaded on first threaded portion 36 to secure the threaded connector 34 to housing 6. A plastic hexagonal nut 44 is threaded on the second threaded portion 40 of threaded connector 34, thereby securing the corrugated tubular member C to the first end A. Hexagonal nut 44 is supported on tubular member C by an annular collar (not shown) formed on the end thereof. The three-lead cable 4 is connected to metallic contacts (not shown) extending downwardly from the female plug 28 in a conventional manner. The conductive oxygen line 2 includes an externally threaded cap 46 for securing oxygen line 2 to oxygen coupler assembly 48.

The oxygen coupler assembly 48 includes a pair of elbows 50 and 52, an oxygen coupler 54 and a bracket 56. Elbows 50 and 52 each include first ends 51 and 53, respectively, having an internally threaded opening formed therein and second ends 55 and 57, respectively, having an externally threaded projection extending therefrom. Oxygen coupler 54 is threaded on the externally threaded projection of second end 57. A sealant is applied at each juncture between oxygen line 2 and oxygen coupler 54 to form an airtight passageway extending therebetween.

Oxygen coupler 54 includes a head 58 and a body 60. The head 58 has an outer diameter greater than that of body 60. A displaceable pin 62 is positioned in an opening formed in head 58. Only upon depression of pin 62 is oxygen permitted to flow through oxygen coupler 54. The oxygen coupler 54 is of the type distributed by Medical Fittings, Inc. under Model No. 2150.

Bracket 56 includes a pair of L-shaped members 64 and 66 having openings formed in each end thereof, a plate 68 and a substantially U-shaped element 70. The height of plate 68 is equal to or slightly greater than the height of opening 16 thus preventing the oxygen coupler assembly 48 from moving in a vertical direction in housing 6. The U-shaped element secures oxygen coupler 54 to plate 68 at opposite ends thereof. A clear plate 72 includes a pair of openings 74 and 76 positioned adjacent the upper and lower edges thereof. An opening 78 is formed in the center of plate 72. A lip 80 surrounds opening 78. The surface of head 58 directly adjacent body 60 rests on lip 80 and face 81 of head 58 extends in substantially the same plane as front surface 83 of plate 72. Cover plate 72 has substantially the same dimensions as opening 16 and fits therein.

Cover plate 82 has a pair of outer openings 84 (only one of which is shown) positioned adjacent the upper and lower edges thereof and a pair of inner openings 86 (only one of which is shown) located directly adjacent corresponding openings 84. A screw is inserted in each of inner openings 86, the corresponding openings 74 and 76 of plate 72 and the openings formed in L-shaped elements 64 and 66 and is mated with a corresponding nut to secure the cover plate 82 and plate 72 to bracket 56. A screw is inserted in each of the outer openings 86 and corresponding internally threaded openings 88 (only one of which is shown) formed in lip 26 thereby securing the front cover plate 82 to the housing 6. A rear cover plate (not shown) is secured to a recessed lip formed in the rear portion of the housing 6 in a similar manner as front cover plate 82.

Second end B is constructed in an identical manner as that of first end A. Accordingly, second end B will not be described in detail.

METHOD OF OPERATION OF THE PREFERRED EMBODIMENT OF THE PRESENT INVENTION

The preferred method of operation of an apparatus formed in accordance with the principles of the present invention will now be described.

FIGS. 4 AND 5

Referring to FIG. 4, first end A is positioned adjacent the individual D situated in a hazardous region and in need of medical assistance. The attending medical personnel such as one or more paramedics connect one end of sensor unit E to the individual and the other end to female plug 28. Further, the assisting medical personnel secure one end of oxygen administering unit F around the air passageways of the individual and the other end to oxygen coupler 54 thereby displacing pin 62 and permitting oxygen to flow from the oxygen line through the oxygen coupler 54 to the oxygen administering unit F. Once the assisting paramedic has connected the sensor unit E and the oxygen administering unit F to the individual, he immediately leaves the hazardous region and returns to a safe area remote therefrom.

Figure 5:
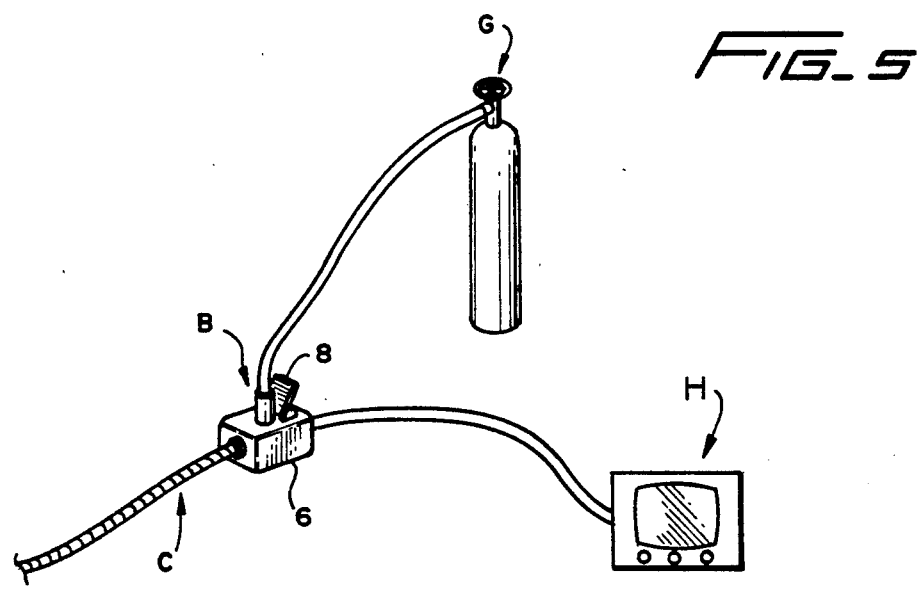
FIG. 5 is a perspective view of the other end of the preferred embodiment of the present invention connected to an oxygen storage tank and an electrocardiogram monitoring unit.

Referring to FIG. 5, the second end B is positioned in a safe area removed from the hazardous region. An oxygen storage unit G is connected to the oxygen coupler 54 of second end B thereby displacing pin 62 permitting oxygen to flow therethrough. Accordingly, once the valve of the oxygen storage tank G is opened, oxygen will flow from the storage tank G to the individual D. A monitoring unit H is connected to the female plug 28 of second end B. Thus, the signal provided by sensor unit E representing the ability of the individual's heart to transmit a cardiac impulse is displayed on electrocardiogram monitoring unit H. Ends A and B may be connected simultaneously or end A can be connected first followed by end B or the reverse thereof. Further, because ends A and B are interchangeable, end A may be positioned in an area remote from the individual and end B can be positioned adjacent the individual. Thus, the attending paramedic need not waste precious time determining which end should be positioned adjacent the individual.

It is readily apparent from the above discussion, that the preferred embodiment of the present invention permits medical personnel to administer aid to a patient situated in a hazardous region as well as monitor the physiological condition of the individual from a safe area remote therefrom. Although in the preferred embodiment the aid administered to the individual is oxygen, it will be readily appreciated that other aid may be rendered to the individual such as providing him with anesthesia, medicine or the like. Similarly, while the preferred embodiment monitors the cardiac impulse of an individual's heart, it will be readily appreciated by one of ordinary skill in the art that other physiological conditions of the patient may be monitored such as blood pressure and the like.

While this invention has been described as having a preferred design, it is understood that it is capable of further modifications, uses and/or adaptions of the invention, following in general the principle of the invention, and including such departures from the present disclosure as come within known or customary practice in the art in which the invention pertains, and as may be applied to the central features hereinbefore setforth, and fall within the scope of the invention of the limits of the appended claims.

I claim:

1. An apparatus for permitting medical personnel to attend to a patient from a remote location, comprising:
   a) a conduit having first and second ends, said first end being removed from said second end;
   b) first connecting means for connecting a health aid storage unit and a physiological condition monitoring unit to said first end of said conduit;
   c) second connecting means for connecting a health aid administering unit and a physiological condition sensor unit to said second end of said conduit;
   d) said conduit including a first transmission line means for transmitting a health aid from said first connecting means to said second connecting means, said conduit further including a second transmission line means for transmitting a signal indicating at least one physiological condition of the patient from said second connecting means to said connecting means; and,
   e) at least one of said first transmission line means and said second transmission line means having means for conveying a fluid.

2. An apparatus as in claim 1, wherein:
   a) said first connecting means includes a first health aid coupling means for coupling the health aid storage unit to said first end and a first sensor coupling means for coupling the physiological condition monitoring unit to said first end, said first connecting means further includes a first housing means for housing said first health air coupling means and said first sensor coupling means.

3. An apparatus as in claim 2, wherein:
   a) said second connecting means includes a second health aid coupling means for coupling the health air administering unit to said second end and a second sensor coupling means for coupling the physiological condition sensor unit to said second end, said second connecting means further includes a second housing means for housing said second health aid coupling means and said second sensor coupling means.

4. An apparatus as in claim 3, wherein:
   a) at least a portion of said first health air coupling means extends substantially perpendicular to at least a portion of said first sensor coupling means; and,
   b) at least a portion of said second health air coupling means extends substantially perpendicular to at least a portion of said second sensor coupling means.

5. An apparatus as in claim 3, wherein:
   a) said first and second health aid coupling means each include an oxygen coupler; and,
   b) said first and second sensor coupling means each include a female connecting plug.

6. An apparatus as in claim 5, wherein:
   a) each of said oxygen couplers include a pin and means for displacing said pin between a first position for permitting oxygen to flow therethrough and a second position for preventing the flow of oxygen therethrough.

7. An apparatus as in claim 1, wherein:

a) said first connecting means includes means for interchangeably connecting a first set of units including the health aid storage unit and the physiological condition monitoring unit and a second set of units including the health aid administering unit and the physiological condition sensor unit to said first end of said conduit; and, b) said second connecting means includes means for interchangeably connecting the first set of units and the second set of units to said second end of said conduit.

8. An apparatus as in claim 1, wherein:

a) said conduit includes a corrugated tubular member positioned intermediate said first connecting means and said second connecting means, said first transmission line means and said second transmission line means are disposed in said corrugated tubular member.

9. An apparatus as in claim 1, wherein:

a) said first connecting means includes a first health aid coupling means for coupling the health aid storage unit to said first end and a first sensor coupling means for coupling a monitoring unit to said first end, said first connecting means further includes a first housing means for housing said first health aid coupling means and said first sensor coupling means;

b) said second connecting means includes a second health aid coupling means for coupling the health aid administering unit to said second end and a second sensor coupling means for coupling the sensor unit to said second end, said second connecting means further includes a second housing means for housing said second health aid coupling means and said second sensor coupling means;

c) each of said first and second health aid coupling means and said first and second sensor coupling means includes an operating face; and, d) lid means is operably associated with each of said operating faces, each of said lid means includes a cover and means for adjustably positioning said cover between a first position exposing a corresponding operating face and a second position covering the corresponding operating face.

10. An apparatus for permitting medical personnel to attend to a patient from a remote location, comprising:

a) a conduit having first and second ends, said first end being removed from said second end;

b) first connecting means for interchangeably connecting a first set of units including a health aid storage unit and a physiological condition monitoring unit and a second set of units including a health aid administering unit and a physiological condition sensor unit to said first end of said conduit;

c) second connecting means for interchangeably connecting the first set of units and the second set of units to said second end of said conduit; and, d) said conduit including a first transmission line means for transmitting a health aid between said first connecting means and said second connecting means, said conduit further including a second transmission line means for transmitting a signal indicating at least one physiological condition of the patient between said first connecting means and said second connecting means.

11. An apparatus as in claim 10, wherein:

a) at least one of said first transmission line means and said second transmission line means includes means for conveying a fluid.

12. An apparatus as in claim 10, wherein:

a) said first connecting means includes means for connecting the health aid administering unit to said first end of said conduit independent of the physiological condition sensor unit.

13. An apparatus as in claim 10, wherein:

a) said first connecting means includes a first oxygen coupler and a first female connecting plug, said first connecting means further includes a first housing means for housing said first oxygen coupler and said first female connecting plug; and, b) said second connecting means includes a second oxygen coupler and a second female connecting plug, said second connecting means further includes a second housing means for housing said second oxygen coupler and said second female connecting plug.

14. An apparatus for permitting medical personnel to attend to a patient from a remote location, comprising:

a) conduit having first and second ends, said first end being removed from said second end;

b) first connecting means for interchangeably connecting a first set of units including at least one of a health aid storage unit and a physiological condition monitoring unit and a second set of units including at least one of a health aid administering unit and a physiological condition sensor unit to said first end of said conduit;

c) second connecting means for interchangeably connecting the first set of units and the second set of units to said second end of said conduit; and, d) said conduit including at least one of a first transmission line means for transmitting a health aid between said first connecting means and said second connecting means and a second transmission line means for transmitting a signal indicating at least one physiological condition of the patient between said first connecting means and said second connecting means.

15. An apparatus for permitting medical personnel to attend to a patient from a remote location, comprising:

a) a conduit having first and second ends, said first end being removed from said second end;

b) first connecting means for connecting a health aid administering unit to said first end of said conduit and a physiological condition sensor unit to said first end of said conduit independent of the health aid administering unit;

c) second connecting means for connecting a health aid storage unit and a physiological condition monitoring unit to said second end of said conduit; and, d) said conduit including a first transmission line means for transmitting a health aid from said second connecting means to said first connecting means, said conduit further including a second transmission line means for transmitting a signal indicating at least one physiological condition of the patient from said first connecting means to said second connecting means.

16. An apparatus as in claim 15, wherein:

a) said first connecting means includes means for interchangeably connecting a first set of units including the health aid storage unit and the physiological condition monitoring unit and a second set of units including the health aid administering unit and the physiological condition sensor unit to said first end of said conduit; and,
b) said second connecting means includes means for interchangeably connecting the first set of units and the second set of units to said second end of said conduit.

17. An apparatus as in claim 15, wherein:
a) said second connecting means includes means for connecting the health aid storage units to said second end of said conduit independent of the physiological condition monitoring unit.

18. An apparatus as in claim 15, wherein:
a) at least one of said first and second transmission line means includes means for conveying a fluid.

19. A method for permitting medical personnel to attend to a patient located in a hazardous area from a safe are remote from the hazardous area, comprising the steps of:
a) providing a health aid storage unit, a health aid administering unit, a sensor unit and a monitoring unit;
b) providing a conduit including a first transmission line means for transmitting a health aid from the health aid storage unit to the health aid administering unit and a second transmission line means for transmitting a signal indicating at least one physiological condition of the patient from the sensor unit to the monitoring unit, the conduit having first and second ends;
c) positioning the first end of the conduit means remote from the patient;
d) positioning the second end of the conduit means adjacent the patient;
e) connecting the health aid storage unit and the monitoring unit to the first end of the conduit;
f) connecting the health aid administering unit to the second end of the conduit; and,
g) connecting the sensor unit to the second end of the conduit means independent of the health aid administering unit.

20. A method as in claim 19, further including the steps of:
a) transmitting oxygen from the health aid storage unit to the health aid administering unit; and,
b) transmitting a signal representing ability of the heart of the patient to transmit a cardiac impulse from the sensor unit to the monitoring unit.

* * * * *